(12) United States Patent
Tanaka et al.

(10) Patent No.: US 8,449,869 B2
(45) Date of Patent: May 28, 2013

(54) ARTIFICIAL NAIL COMPOSITION HAVING IMPROVED ADHESION PROPERTY

(75) Inventors: Hisaki Tanaka, Kyoto (JP); Mikito Deguchi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 13/209,654

(22) Filed: Aug. 15, 2011

(65) Prior Publication Data

US 2011/0297171 A1  Dec. 8, 2011

Related U.S. Application Data

(62) Division of application No. 12/457,284, filed on Jun. 5, 2009, now abandoned.

(30) Foreign Application Priority Data

Aug. 29, 2008  (JP) .................................. 2008-221249

(51) Int. Cl.
*A61K 8/00* (2006.01)
*A61K 8/02* (2006.01)
*A45D 7/00* (2006.01)

(52) U.S. Cl.
USPC .............................. 424/61; 424/401; 132/200

(58) Field of Classification Search
None
See application file for complete search history.

(56) References Cited

U.S. PATENT DOCUMENTS

| 4,615,348 A | * | 10/1986 | Nakata et al. | .................... 132/73 |
| 5,367,002 A | * | 11/1994 | Huang et al. | .................... 523/116 |
| 2001/0056133 A1 | * | 12/2001 | Montgomery et al. | ........ 523/113 |
| 2010/0041786 A1 | * | 2/2010 | Qian | ............................. 522/154 |

FOREIGN PATENT DOCUMENTS

| EP | 0 424 112 | | 10/1990 |
| EP | 0424112 | * | 10/1990 |
| EP | 1262530 | * | 12/2002 |
| JP | 2000-232912 | | 8/2000 |
| WO | 00/76366 | | 12/2000 |
| WO | 2007/017152 | | 2/2007 |
| WO | 2007/079070 | | 7/2007 |
| WO | 2007/079166 | | 7/2007 |

OTHER PUBLICATIONS

Chen et al. "Quantum Yield Converstion of the Photoinitiator Camphorquinone", Dental Materials, 23, 2007, pp. 655-664.*
Chen et al., Quantum Yield of Conversion of the Dental Photoinitiator Camphorquinone, Dental Materials, 23, 2007, 655-664.
Journal of Clinical and Experimental Medicine, Ishiyaku Publishers, Inc., Jan. 27, 1996, vol. 176, No. 4, p. 242.

* cited by examiner

*Primary Examiner* — Daniel Sullivan
*Assistant Examiner* — Melissa Javier
(74) *Attorney, Agent, or Firm* — Wenderoth, Lind & Ponack, L.L.P.

(57) ABSTRACT

An object of the present invention is to provide an artificial nail composition which can improve adhesion between a natural nail and an artificial nail, and also can suppress exfoliation or detachment.

The artificial nail composition comprises:

(a) a compound having at least one radical polymerizable unsaturated double bond in the molecule, (b) an acidic phosphorus compound having at least one radical polymerizable unsaturated double bond in the molecule, and (c) a radical polymerization initiator.

2 Claims, No Drawings ic nail composition which is formed on a
ARTIFICIAL NAIL COMPOSITION HAVING IMPROVED ADHESION PROPERTY This application is a Divisional Application of application Ser. No. 12/457,284, filed Jun. 5, 2009 now abandoned.

BACKGROUND OF THE INVENTION

1. Field of the Invention

The present invention relates to an artificial nail composition having improved adhesion property, and more particularly to an artificial nail composition which is formed on a natural nail, and is used for the purpose of imparting special aesthetic appearance, strengthening a fragile nail for a paramedical purpose, and regenerating and protecting a deformed and discolored nail by a step of applying the composition on natural nail surfaces, followed by polymerization, or a step of applying the composition on natural nail surfaces and adjusting a color tone by means of form formation or lamination. The present invention also relates to an artificial nail composition which can improve adhesion between a natural nail and an artificial nail, and can also suppress exfoliation of a laminated artificial nail.

2. Description of the Related Art

Nail art means makeup or decoration of nails of the hands and feet. A shop for the nail art is called a nail salon and a nail art technician is called a nailist.

Various nail art goods are commercially available and there are many women who perform nail art with a skill equivalent to a professional.

It is possible to confirm by a mummy that there has already existed a culture of coloring nails in ancient Egypt of about 3,000 to 4,000 BC. It is known that nails of a higher ranked person were colored with deeper colors using a vegetable dye such as henna.

It is considered that current nail art became popular in Europe about the 18th century. In China, in the Tang Period, Yang Guifei performed coloring of nails. It is known that coloring of nails was transmitted to Japan in the Heian era and nails were colored using a juice of flowers such as *Impatiens balsamina* and safflower. It is known that prostitutes performed coloring of nails in the Edo era.

In the 19th century in USA, a lacquer coating material for an automobile was invented and a currently used manicure was developed by application of this technique.

Although a long time is required for application in a nail art, handling is conducted with only the finger-tips and no water is required for the application, therefore, a nail salon can be opened without requiring a large space. Accordingly, managing is carried out using, in addition to specialty stores, a portion of facilities such as hair salons, drugstores, cosmetic salons, fashion-business buildings, beauty vocational schools, individual's houses and the like and, thus, nail art has generally become popular.

A manicure using a lacquer coating material is widely used at present but is inferior in adhesion with a natural nail, and has a problem that it is exfoliated or detached within a short period after the application. For this reason, an artificial nail material using a dental normal temperature polymerization resin was developed.

Recently, a gel nail having improved odor stimulation or operability of the artificial nail material using the dental normal temperature polymerization resin has dominated the market.

However, adhesion of the artificial nail material to natural nails, which was a problem in the manicure using the lacquer coating material, is not sufficiently improved.

Furthermore, it is considered that exfoliation caused by low adhesion between a natural nail and an artificial nail, and exfoliation between laminated artificial nails not only gives aesthetic discomfort, but also includes a hygienic problem and is a main cause for infectious diseases of persons to be subjected to the application of an artificial nail and, thus, there is a need for the development of an artificial nail material having high adhesion.

JP-A No. 2-1779 discloses a pre-treated composition which enhances adhesion of at least one of an adhesive, a coating and a complex to a protein substrate, and a method for preparing a composition which enhances adhesion of at least one of an adhesive, a coating and a complex to a protein substrate. The publication discloses that a composition containing a solvent miscible with water and an unsaturated carboxylic acid compound is effective for adhesion to a keratinous structure, but has a problem such as insufficient adhesion.

SUMMARY OF THE INVENTION

An object of the present invention is to improve adhesion between a natural nail and an artificial nail, and also to suppress exfoliation or detachment in an artificial nail composition. Another object of the present invention is to suppress exfoliation or detachment of a laminated structure of an artificial nail and an artificial nail. A still another object of the present invention is to provide an artificial nail composition which does not require a primer for imparting adhesion, or an adhesive, and also to provide a primer for imparting adhesion, or an adhesive composition.

The present invention provides an artificial agent comprising (a) a compound having at least one radical polymerizable unsaturated double bond in the molecule, (b) an acidic phosphorus compound having at least one radical polymerizable unsaturated double bond in the molecule, and (c) a radical polymerization initiator.

The present invention also provides (2) the artificial nail composition according to (1), comprising (a) 0.1 to 98.5 parts by weight of a compound having at least one radical polymerizable unsaturated double bond in the molecule, (b) 0.1 to 98.5 parts by weight of an acidic phosphorus compound having at least one radical polymerizable unsaturated double bond in the molecule, and (c) 0.01 to 10 parts by weight of a radical polymerization initiator.

The present invention also provides (3) the artificial nail composition according to (1) or (2), wherein (b) the acidic phosphorus compound having at least one radical polymerizable unsaturated double bond in the molecule has a P—OH bond.

The present invention also provides (4) the artificial nail composition according to any one (1) to (3), wherein (b) the acidic phosphorus compound having at least one radical polymerizable unsaturated double bond in the molecule has at least one kind selected from the group consisting of a phosphoric acid monoester group, a phosphoric acid diester group, a phosphonic acid group, a phosphonic acid monoester group, a phosphorous acid monoester group, a phosphinic acid group and a pyrophosphoric acid group.

According to the present invention, it is possible to improve adhesion between a natural nail and an artificial nail and to suppress exfoliation or detachment in an artificial nail composition, and also to suppress exfoliation or detachment of a laminated structure of an artificial nail and an artificial nail and to maintain a special aesthetic appearance over a long period. Furthermore, it is possible to solve a hygienic problem of a person to be subjected to the application of an artificial nail.

It is also possible to suppress wasted time for a person who applies an artificial nail and a person to be subjected to the application of an artificial nail by providing an artificial nail composition which does not require a primer for imparting adhesion, or an adhesive.

DETAILED DESCRIPTION OF THE INVENTION

The compound (a) having at least one radical polymerizable unsaturated double bond in the molecule in the present invention can be used from among known monofunctional and polyfunctional polymerizable monomers. Typical examples of the compound, which is preferably used, include polymerizable monomers having an acryloyl group and/or a methacryloyl group. In the present invention, both an acryloyl group-containing polymerizable monomer and a methacryloyl group-containing polymerizable monomer are comprehensively expressed by (meth)acrylate or (meth)acryloyl.

Specific examples are as follows:
monofunctional monomers such as methoxyethylene glycol (meth)acrylate, methoxypolyethylene glycol (meth)acrylate, phenoxyethylene glycol (meth)acrylate, phenoxypolyethylene glycol (meth)acrylate, 2-hydroxy-3-phenoxypropyl (meth)acrylate, 2-(meth)acryloyloxyethylsuccinic acid, 2-(meth) acryloyloxyethylphthalic acid, 2-(meth) acryloyloxypropylhexaphthalic acid, stearyl (meth)acrylate, and 3-chloro-2-hydroxypropyl (meth)acrylate;
difunctional monomers such as 1,6-hexanediol di(meth)acrylate, 1,9-nonanediol di(meth)acrylate, 1,10-decanediol di(meth)acrylate, neopentyl glycol di(meth)acrylate, 2-methyl-1,8-octanediol di(meth)acrylate, glycerin di(meth)acrylate, ethylene glycol di(meth)acrylate, polyethylene glycol di(meth)acrylate, propylene glycol di(meth)acrylate, polypropylene glycol di(meth)acrylate, ethoxylated polypropylene glycol di(meth)acrylate, ethoxylated propylene glycol di(meth)acrylate, ethoxylated bisphenol A di(meth)acrylate, propoxylated bisphenol A di(meth)acrylate, propoxylated ethoxylated bisphenol A di(meth)acrylate, and tricyclodecane dimethanol di(meth)acrylate; and
tri- or higher functional monomers such as trimethylolpropane tri(meth)acrylate, ethoxylated trimethylolpropane tri(meth)acrylate, ethoxylated glycerin tri(meth)acrylate, ditrimethylolpropane tetra(meth)acrylate, pentaerythritol tri(meth)acrylate, pentaerythritol tetra(meth)acrylate, propoxylated pentaerythritol tetra(meth)acrylate, ethoxylated pentaerythritol (meth)acrylate, dipentaerythritol hexa(meth)acrylate, and ethoxylated isocyanuric acid tri (meth)acrylate There is no particular limitation on use of polymerizable monomers other than the above (meth)acrylate-based polymerizable monomers, for example, oligomers or polymers having at least one polymerizable group in the molecule according to the purposes of an artificial nail composition. It is possible to use a substituent such as an acidic group, a fluoro group or the like in the same molecule.

In the present invention, the compound (a) having at least one radical polymerizable unsaturated double bond in the molecule includes not only a single component, but also a mixture of a plurality of polymerizable monomers. When the polymerizable monomer has very high viscosity at room temperature, or the polymerizable monomer is solid, it is preferred to use as a mixture of the polymerizable monomer in combination with a polymerizable monomer having low viscosity. This combination is not limited to a combination of two kinds, or may be a combination of three or more kinds.

The blending ratio of the compound (a) having at least one radical polymerizable unsaturated double bond in the molecule in the present invention is from 0.1 to 98.5 parts by weight, preferably from 0.5 to 90.0 parts by weight in the case of an artificial nail composition for coating, building up or an adhesive, and preferably from 0.1 to 30 parts by weight for an artificial nail composition for a primer.

Regarding the acidic phosphorus compound (b) having at least one radical polymerizable unsaturated double bond in the molecule in the present invention, a functional group having a radical polymerizable unsaturated double bond includes a (meth)acryloyl group, an allyl group, a vinyl group, a cyanoacryloyl group, a propenyl group, a butenyl group or the like, and a (meth)acryloyl group and a vinyl group are particularly preferred.

Furthermore, the compound in which the acidic phosphorus compound having at least one radical polymerizable unsaturated double bond in the molecule has a P—OH bond is a compound having at least one kind selected from a phosphoric acid monoester group, a phosphoric acid diester group, a phosphonic acid group, a phosphonic acid monoester group, a phosphorous acid monoester group, a phosphinic acid group, and a pyrophosphoric acid group, and is particularly preferably a compound having a phosphoric acid monoester group, a phosphoric acid diester group or a phosphonic acid group. Specific examples thereof include:

[Chemical Formula 1]

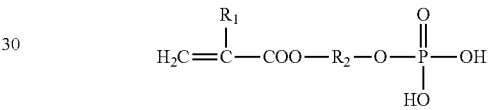

wherein $R_1$ represents a hydrogen atom or a methyl group; and $R_2$ represents an alkylene group having 1 to 20 carbon atoms which may have a substituent. Typical compound includes 2-methacryloxyethyl phosphate (2-MEP):

[Chemical Formula 2]

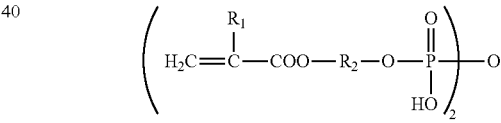

wherein $R_1$ represents a hydrogen atom or a methyl group, and $R_2$ represents an alkylene group having 1 to 20 carbon atoms which may have a substituent. Typical compound thereof includes di(2-methacryloxyethyl)-phosphate (Di-MEP):

[Chemical Formula 3]

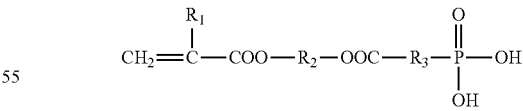

wherein $R_1$ represents a hydrogen atom or a methyl group, $R_2$ represents an alkylene group having 5 to 10 carbon atoms, and $R_3$ represents an alkylene group having 1 to 6 carbon atoms. Typical compound includes 6-methacryloxy hexylphosphonoacetate (6-MHPA).

The radical polymerization initiator (c) in the present invention can be used in the blending ratio of 0.01 to 10 parts by weight, and the blending ratio is preferably from 0.1 to 5 parts by weight. As the radical polymerization initiator, known thermopolymerization and photopolymerization initiators can be used. Examples of the photopolymerization initiator include benzoinethers, benzylketals, α-dialkoxyacetophenones, α-hydroxyalkylphenones, α-aminoalkylphenone, acylphosphine oxides, benzophenones, thioxanthones, titanocenes and the like, and 2-hydroxy-2-methylpropiophenone is preferred.

It is also preferred to use the above radical polymerization initiator in combination with a photopolymerization promoter. When tertiary amines are used as the photopolymerization promoter, it is preferred to use a compound in which a nitrogen atom is directly substituted on an aromatic group. It is possible to use, as the photopolymerization promoter, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, N,N-dihydroxyethyl-p-toluidine, p-dimethylaminophenylalcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, 2,2'-(n-butylimino)dimethanol and the like; barbituric acids such as 5-butylbarbituric acid, 1-benzyl-5-phenylbarbituric acid and the like, and metal salts thereof such as sodium salt, calcium salt and the like; and tin compounds such as dibutyltin diacetate, dibutyltin dimaleate, dioctyltin dimaleate, dioctyltin dilaurate, dibutyltin dilaurate, dioctyltin diversatate, dioctyltin S,S'-bis-isooctyl mercaptoacetate, tetramethyl-1,3-diacetoxydistannoxane and the like. Among these photopolymerization promoters, at least one can be selected and used, and two or more kinds of them can also be used by mixing them. The amounts of the initiator and promoter to be added can be appropriately selected.

For the purpose of improving photopolymerization promoting ability, it is effective to add, in addition to the tertiary amines, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid, dimethylolpropionic acid and the like.

Specific examples of the thermopolymerization initiator include organic peroxides such as benzoyl peroxide, parachlorobenzoyl peroxide, 2,4-dichlorobenzoyl peroxide, acetyl peroxide, lauroyl peroxide, tertiary butyl peroxide, cumen hydroperoxide, 2,5-dimethylhexane-2,5-dihydroperoxide, methyl ethyl ketone peroxide, tertiary butyl peroxybenzoate and the like; and azo compounds such as azobisisobutyronitrile, methyl azobisisobutyrate, azobiscyanovaleric acid and the like.

The polymerization can be carried out at a normal temperature by using the above organic peroxide in combination with an amine compound. As such the amine compound, a secondary or tertiary amine in which an amine group is bonded with an aryl group is preferably used in view of curing promotion. For example, N,N-dimethyl-p-toluidine, N,N-dimethylaniline, N,N-β-hydroxyethyl-aniline, N,N-di(β-hydroxyethyl)-aniline, N,N-di(β-hydroxyethyl)-p-toluidine, N-methyl-aniline, and N-methyl-p-toluidine are preferred.

It is also preferred to use the combination of the organic peroxide and the amine compound in combination with sulfinate or boride. Examples of sulfinates include sodium benzenesulfinate, lithium benzenesulfinate, sodium p-toluenesulfinate and the like. Examples of the boride include sodium salt, lithium salt, potassium salt, magnesium salt, tetrabutylammonium salt, tetramethylammonium salt and the like of trialkylphenylboron, trialkyl(p-fluorophenyl)boron (alkyl group is an n-butyl group, an n-octyl group, an n-dodecyl group or the like) and the like. Organic boron compounds such as tributylborane, tributylborane partial oxide and the like, which react with oxygen or water to generate a radical, can also be used as an organic metal type polymerization initiator.

The artificial nail composition of the present invention can be optionally blended with known various additives. Examples of additives include polymerization inhibitors, colorants, discoloration preventing agents, fluorescent agents, ultraviolet absorbers, antibacterial agents, volatile organic solvents and the like.

EXAMPLES

The present invention will be specifically described by way of Examples and Comparative Examples. The present invention is not limited to these Examples.
Abbreviations (Chemical Name) Used in Examples
(a) Compound having at least one radical polymerizable unsaturated double bond in the molecule
9PG: Nonapropylene glycol dimethacrylate
Bis-EMA: Ethoxylated propylene glycol dimethacrylate (average ethylene oxide addition mol number=17)
(b) Acidic phosphorus compound having at least one radical polymerizable unsaturated double bond in the molecule
2-MEP: 2-methacryloxyethyl phosphate
Di-MEP: Di(2-methacryloxyethyl)-phosphate
6-MHPA: 6-methacryloxyhexyl phosphonoacetate
(c) Radical polymerization initiator
2HMPP: 2-hydroxy-2-methylpropiophenone
Other Additives
R972: Ultrafine silica particles (viscosity adjustor)
Apparatus Used for Test
Instron universal testing machine [manufactured by Instron Ltd.]
Preparation of Artificial Nail Composition Components of an artificial nail composition were weighed according to the formulation in Table 1 and then mixed under an atmospheric pressure at 23° C. for 15 hours to obtain uniform liquid artificial nail compositions of Examples 1 to 12 and Comparative Examples 1 to 4.

TABLE 1

Table for Preparation of Artificial Nail Composition and Results of Shear Adhesion Test

| Examples and Comparative Examples | Name and amount [parts by weight] of components | | | | | | | Shear adhesive strength [MPa] |
|---|---|---|---|---|---|---|---|---|
| | (a) | | (b) | | | (c) | | |
| | 9PG | Bis-EMA | 2-MEP | Di-MEP | 6-MHPA | 2HMPP | R972 | |
| Example 1 | 30.00 | 66.0 | 2.0 | 0.00 | 0.00 | 0.50 | 1.50 | 4.0 |
| Example 2 | 30.00 | 66.0 | 2.0 | 2.0 | 0.00 | 0.50 | 1.50 | 3.9 |

TABLE 1-continued

Table for Preparation of Artificial Nail Composition and Results of Shear Adhesion Test

| Examples and Comparative Examples | (a) 9PG | (a) Bis-EMA | (b) 2-MEP | (b) Di-MEP | (b) 6-MHPA | (c) 2HMPP | R972 | Shear adhesive strength [MPa] |
|---|---|---|---|---|---|---|---|---|
| Example 3 | 30.00 | 66.0 | 2.0 | 0.00 | 2.0 | 0.50 | 1.50 | 4.2 |
| Example 4 | 28.00 | 65.00 | 4.00 | 0.00 | 0.00 | 1.00 | 2.00 | 4.4 |
| Example 5 | 28.00 | 65.00 | 0.00 | 4.00 | 0.00 | 1.00 | 2.00 | 4.1 |
| Example 6 | 28.00 | 65.00 | 0.00 | 0.00 | 4.00 | 1.00 | 2.00 | 4.8 |
| Example 7 | 29.00 | 68.00 | 0.00 | 0.30 | 0.00 | 1.00 | 1.70 | 3.4 |
| Example 8 | 23.00 | 62.00 | 0.00 | 11.00 | 0.00 | 1.00 | 3.00 | 3.9 |
| Example 9 | 18.00 | 56.00 | 0.00 | 22.00 | 0.00 | 1.00 | 3.00 | 4.9 |
| Example 10 | 7.00 | 45.00 | 0.00 | 44.00 | 0.00 | 1.00 | 3.00 | 4.0 |
| Example 11 | 3.00 | 7.00 | 0.00 | 88.00 | 0.00 | 1.00 | 1.00 | 4.3 |
| Example 12 | 1.00 | 1.00 | 0.00 | 97.00 | 0.00 | 1.00 | 0.00 | 4.4 |
| Comparative Example 1 | 30.00 | 68.00 | 0.00 | 0.00 | 0.00 | 1.00 | 1.00 | 0.5 |
| Comparative Example 2 | 28.00 | 67.00 | 0.09 | 0.00 | 0.00 | 1.00 | 3.95 | 1.5 |
| Comparative Example 3 | 28.00 | 67.00 | 0.00 | 0.09 | 0.00 | 1.00 | 3.95 | 1.5 |
| Comparative Example 4 | 28.00 | 67.00 | 0.00 | 0.00 | 0.09 | 1.00 | 3.95 | 1.8 |

Test of Adhesion of Artificial Nail Composition to Keratin Substrate

A keratin substrate was used in place of a natural nail. The keratin substrate was used by embedding in an epoxy resin. The embedded keratin substrate was polished while pouring water using a #1200 SiC abrasive paper to obtain a smoothed surface. After ultrasonic cleaning and further air drying, an adherend was obtained.

To the polished adhesion surface, a double-stick tape with a hole having a diameter of 4 mm was applied to define the adhesion surface. Then, a plastic mold having a diameter of 4 mm and a height of 2 mm was fixed to a frame of adhesion defined surface and the artificial nail composition thus prepared was filled into the mold. After shielding the air with a cover glass, the artificial nail composition was irradiated with ultraviolet rays from a UV light (36 W) for a commercially available gel nail for 180 seconds thereby curing the artificial nail composition.

A test of adhesion to each artificial nail composition was repeated 6 times. Twenty four hours after storage at 23° C. under an atmospheric pressure, the adhesion test was carried out.

In the measurement of the adhesion strength, using a Universal testing machine (Instron, Model 5550), a shear adhesion strength was measured under the conditions of a crosshead speed of 1 mm/min. The measurement results are also shown in Table 1.

As is apparent from the results shown in Table 1, the artificial nail compositions of the present invention are excellent in a shear adhesive strength to the keratin substrate when compared with the artificial nail compositions of Comparative Examples.

Examination by Monitor for Evaluation of Adhesion Durability of Artificial Nail Composition In order to evaluate the adhesion durability of the artificial nail compositions of the present invention, each of the artificial nail compositions of Example 1, Example 4, Example 8, Example 10, Example 11 and Comparative Example 1 as well as commercially available products "AKZENTZ" (manufactured by TAKIGAWA. CO., LTD.) and "NOBILITY" (manufactured by LUNERS) was applied to three subjects, and then retention durability of artificial nails after application was evaluated. Each artificial nail composition was applied by a person authorized by the Japan Nailist Association and a natural nail overlay (clear coat of natural nail) was selected as an application method. After application, a lapsed time until a phenomenon capable of causing considerable deterioration of appearance and function as an artificial nail was confirmed, and details of the phenomenon are shown in Table 2. During 14 days after application, examination was carried out.

TABLE 2

Results of Examination by Monitor for Evaluation of Adhesion Durability of Artificial Nail Composition

| Artificial nail composition | Lapsed day | Details |
|---|---|---|
| Example 1 | 14 days | After lapse of 14 days, considerable deterioration of appearance and function was not recognized. |
| Example 4 | 14 days | After lapse of 14 days, considerable deterioration of appearance and function was not recognized. |
| Example 8 | 14 days | After lapse of 14 days, considerable deterioration of appearance and function was not recognized. |
| Example 11 | 14 days | After lapse of 14 days, considerable deterioration of appearance and function was not recognized. |
| Comparative Example 1 | 2 days | Exfoliation of an artificial nail composition from a free edge was recognized. Falling-off of an artificial nail composition as a result of exfoliation was recognized over the entire adhesion surface. |
| AKZENTZ | 5 days | Partial exfoliation of an artificial nail composition from a free edge was recognized. |
| NOBILITY | 3 days | Partial exfoliation of an artificial nail composition from a free edge was recognized. |

As is apparent from Table 2, the artificial nail composition of the present invention is excellent in adhesion durability.

According to the present invention, there is provided an artificial nail composition having improved adhesion, which can be used for the purpose of strengthening a natural nail, and regenerating and protecting a deformed and discolored nail.

What is claimed is:

1. A method of improving adhesion between a natural nail and an artificial nail, comprising adhering the natural nail and artificial nail to each other with an artificial nail composition comprising:
   (a) a compound having at least one radical polymerizable unsaturated double bond in the molecule;
   (b) at least one acidic phosphorus compound having at least one radical polymerizable unsaturated double bond in the molecule selected from the group consisting of 2-methacryloxyethyl phosphate, di(2-methacryloxyethyl)-phosphate, and 6-methacryloxyhexyl phosphonoacetate; and
   (c) a radical polymerization initiator.

2. The method according to claim 1, wherein the artificial nail composition comprises:
   (a) 0.1 to 98.5 parts by weight of the compound having at least one radical polymerizable unsaturated double bond in the molecule,
   (b) 0.1 to 98.5 parts by weight of the acidic phosphorus compound having at least one radical polymerizable unsaturated double bond in the molecule, and
   (c) 0.01 to 10 parts by weight of the radical polymerization initiator.

* * * * *